United States Patent

Park et al.

[11] Patent Number: 5,973,201
[45] Date of Patent: Oct. 26, 1999

[54] PHENYLACETAMIDE DERIVATIVES

[75] Inventors: No-Sang Park; Young-Sik Jung; Churl-Min Seong, all of Daejeon; Seung-Won Choi, Seoul; Yeon-Joo Choi, Daejeon; Jong-Cheol Lee, Daejeon; Jin-Il Choi, Daejeon; Kwang-Sook Lee, Daejeon; Jae-Yang Kong, Daejeon; Bu-Yeon Lee, Daejeon; Jae-Hong Kim, Daejeon, all of Rep. of Korea

[73] Assignee: Korea Research Institute of Chemical Technology, Rep. of Korea

[21] Appl. No.: 09/077,976

[22] PCT Filed: Dec. 11, 1996

[86] PCT No.: PCT/KR96/00239

§ 371 Date: Jun. 12, 1998

§ 102(e) Date: Jun. 12, 1998

[87] PCT Pub. No.: WO97/21668

PCT Pub. Date: Jun. 19, 1997

[30] Foreign Application Priority Data

Dec. 12, 1995 [KR] Rep. of Korea ............. 95-48617

[51] Int. Cl.$^6$ ............. C07C 233/00; A01N 43/30
[52] U.S. Cl. ............. 564/123; 514/466
[58] Field of Search ............. 564/123; 514/466

[56] References Cited

U.S. PATENT DOCUMENTS

| | | | |
|---|---|---|---|
| 4,313,958 | 2/1982 | LaHann | 564/123 |
| 4,424,205 | 1/1984 | LaHann et al. | 564/123 |
| 5,045,565 | 9/1991 | Gardner et al. | 564/123 |
| 5,242,944 | 9/1993 | Park et al. | 514/466 |

*Primary Examiner*—Louise N. Leary
*Attorney, Agent, or Firm*—Anderson Kill & )lick

[57] ABSTRACT

A phenylacetamide derivative of formula (I) have potent analgesic and anti-inflammatory activities and exhibit less irritability and toxicity:

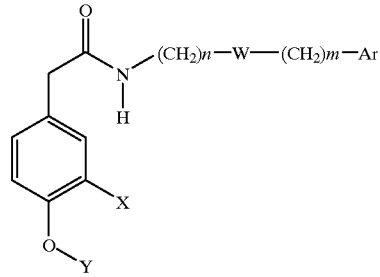

wherein, X, Y, W, n, m and Ar are as defined in the specification.

6 Claims, No Drawings

PHENYLACETAMIDE DERIVATIVES

FIELD OF THE INVENTION

The present invention relates to phenylacetamide derivatives and pharmaceutically acceptable salts thereof, which have potent analgesic and anti-inflammatory activities.

BACKGROUND OF THE INVENTION

Capsaicin, N-vanillyl-trans-8-methyl-6-nonenamide, is a hot substance found in the fruit juice of a plant belonging to the genus Capsicum. U.S. Pat. No. 4,313,958 issued to LaHann, and European Patent No. 0 282 127 granted to Garnder, disclose as having analgesic activities such natural capsaicin and synthetic capsaicin derivatives, e.g., N-{4-(2-aminoethoxy)- 3-methoxybenzyl}amide derivatives.

Also reported in LaHann et al., U.S. Pat. No. 4,424,205; Gardner et al., U.S. Pat. No. 5,045,565; and Park et al., U.S. Pat. No. 5,242,944 are various homovanillic amides, i.e., phenylacetamide derivatives, as having pharmacologically and physiologically activities superior to the conventional capsaicin derivatives. However, each of thoese disclosed in the prior art still exhibits some of the skin irritability and toxicity unique to a capsaicin.

SUMMARY OF THE INVENTION

It is, therefore, a primary object of the present invention to provide a phenylacetamide derivative having potent analgesic and anti-inflammatory activities which is less irritable and toxic.

It is another obbject of the present invention to provide a pharmaceutical composition comprising said compound as an active ingredient.

In accordance with one aspect of the present invention, there is provided et phenylacetamide compound of formula (I) and a pharmaceutically acceptable salt thereof:

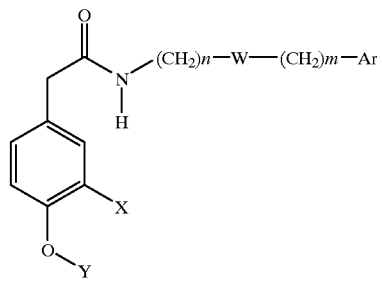

(I)

wherein:
X is hydrogen, halogen, hydroxy or $C_{1-3}$ alkoxy group; and
Y is hydrogen, $C_{3-5}$ hydroxyalkyl, $CH_2CH_2NR^1R^2$ wherein $R^1$ and $R^2$ are each independently hydrogen, $C_{1-3}$ alkyl, $C_{1-3}$ hydroxyalkyl, $C_{1-3}$ aminoalkyl, formyl, $C_{1-3}$ alkylcarbonyl or $C_{1-3}$ alkoxycarbonyl group;
Ar is phenyl or phenyl having one or more substituents selected from the group consisting of $C_{1-5}$ alkyl, halogen, hydroxy, $C_{1-5}$ alkoxy and alkylenedioxy group;
w is an oxygen or sulphur atom;
n is all integer ranging from 1 to 5; and
m is 0 or an integer ranging from 1 to 5.

In accordance with another aspect of the present invention, there is also provided a pharmaceutical composition containing the compound of formula (I) as an active ingredient.

DETAILED DESCRIPTION OF THE INVENTION

The compound of formula (I) is structurally distinct from the phenylacetamide derivatives of the prior art; it has a unique feature that the aralkyl substituent attached to the nitrogen atom carries an ether or thioether group therewithin. Presumably due to this structural feature, the inventive compound of formula (I) possesses a much reduced level of toxicity and skin irritability, while retaining all the analgesic and anti-inflammatory potency. Moreover, the inventive compound exhibits improved physical properties, e.g., improved solubilities in mixed solvents, as compared with the compound of the prior art. It is therefore possible to use the compound of formula (I) or a pharmaceutically acceptable salts thereof as a highly effective analgesic and anti-inflammatory agent.

The inventive compound of formula (I) may form salts when Y is hydrogen or a group containing one or more amine groups. In case when one or more amine groups are present, pharmaceutically acceptable salts thereof may be made using an inorganic acid such as hydrochloric acid, hydrobromic acid, sulfuric acid, sodium hydrogen sulfate, carbonic acid, or using an organic acid such as formic acid, acetic acid, oxalic acid, benzoic acid, citric acid, tartaric acid, gluconic acid, gentisic acid, fumaric acid, lactobionic acid, salicylic acid, acetylsalicylic acid (aspirin). In addition, the compound of formula (I) and a salt thereof may exhibit polymorphism.

The phenylacetamide derivative of formula (I) of the present invention may be prepared in accordance with a process which comprises: (i) reacting a compound of formula (II) with an amine compound of formula (III) to produce a compound of formula (IV), and (ii) reacting the compound of formula (IV) with a compound suitable for constructing a desired substituent Y to provide the compound (I):

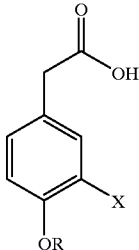

(II)

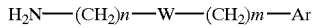

(III)

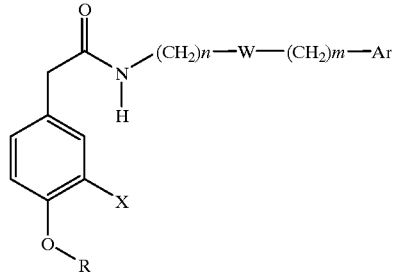

(IV)

wherein:
R is H, $CH_2CH_2Cl$, $CH_2CH_2Br$, $CH_2CH_2N_3$ or $CH_2C_2NH_2$; and m, n, W, X and Ar have the same meanings as defined above.

In the above process, the reaction of the compound of formula (II) with the compound of formula (III) in step (i) may be carried out in the presence of a condensing agent, e.g., dicyclohexylcarbodiimde(DCC), in a suitable solvent, e.g., dichloromethane, acetonitrile or dimethylformamide at a rolar ratio of the compound (II), the compound (II) and the condensing agent ranging from 1.0:0.9:0.9 to 1.0:1.2:1.2 at a temperature ranging from 0 to 50° C. for 0.1 to 5 hours.

Alternatively, the reaction step (i) may be carried out without the use of any solvent in the presence of a catalyst, e.g., molecular sieve 3A, 4A or 5A, preferably 4A, by heating the compound (II) and the compound (III) in a molar ratio ranging fron 1.0:0.9 to 0:1.2 at a temperature ranging from 100 to 180° C. for 1 to 2 hours.

In the reaction step (ii), the compound of formula (IV) having the group R is reacted with a suitable compound to obtain the compound (I) having the desired Y group by any conventional method.

For example, a carbamate group may be introduced by sirring a mixture of the compound (IV), wherein R is $CH_2CH_2NH_2$ and an appropriate chloroformate at room temperature for 1 to 5 hours. And, other group, eg., an amino group may be easily introduced by employing any conventional methods described in the open literature, as shown in more detail in the Examples.

The compounds of formulas (II) and (III) which are used as starting materials in preparing the compound of formula (I) are commercially available, or alternatively they may be synthesized, e.g., according to the processes described in Korean Patent Nos. 60005, 85116, 85117 and 85118.

Representative examples of the phenylacetamide derivatives of formula (I) of the present invention are as follows:
N-{2-(3,4-dimethylphenoxy)ethyl}-4-(2-aminoethoxy)-3-methoxyphenylacetamide;
N-{3-(3,4-dimethylphenoxy)propyl}-4-(2-aminoethoxy)-3-methoxyphenylacetamide;
N-{2-(3,4-dimethylbenzyloxy)ethyl}-4-(2-aminoethoxy)-3-methoxyphenylacetamide;
N-{2-(3,4-dimethylbenzyloxy)ethyl}-4-hydroxy-3-methoxyphenylacetamide;
N-{2-(4-methylthiophenoxy)ethyl}-4-(2-aminoethoxy)-3-methoxyphenylacetamide; and
N-{2-(3,4-dimethylthiophenoxy)ethyl}-4-(2-aminoethoxy)-3-methoxyphenylacetamide.

The novel compounds of formula (I) of the present invention are much less irritable and toxic than the phenylacetamide derivatives of the prior art, when tested for the physiological activities. In addition, they showed considerably increased solubilities, e.g., in a mixed solvent of Tween 80, alcohol and distilled water (1:5:20). therefore, the compounds of formula (I) and pharmaceutically acceptable salts thereof may be used as an effective analgesic and anti-inflammatory agent.

The present invention also includes within its scope phamaceutical compositions comprising one or more of the compound (I) or pharmaceutically acceptable salts thereof as active ingredients, in association with a pharmaceutically acceptable carrier. The term "pharmaceutically acceptable carrier," as used herein, means one or more solids, liquid fillers, diluents or encapsulating materials which are suitable for human or animal administration.

Examples of substances which may be used as the carrier are sugar, starch, cellulose and its derivatives, powdered tragacanth, malt, gelatin, talc, stearic acid, magnesium stearate, calcium sulfate, vegetable oils, polyols, alginic acid, pyrogen-free water, isotonic saline phosphate buffer solutions, cocoa buffer (suppository base), emulsifier as well as other non-toxic pharmaceutically compatible substances used in other pharmaceutical formulations.

Wetting agents and lubricants such as sodium lauryl sulfate, as well as coloring agents, flavoring agents, excipients, tabletting agents, stabilizers, antioxidants and preservatives may be also present. Other compatible additives and ingredients such as pain killers, muscle relaxants may be included in the possible pharmaceutical carrier for use in the compositions of the present invention.

Proper pharmaceutical carriers of the present invention are basically determined by the administration route. The compounds of the present invention may be administered boy injection, orally and topically. If the compound is to be injected, the preferred carrier is sterile, physiological saline having pH 4. If the compound is to be applied topically, the carrier may preferably comprise those suited for use in creams, gels, tapes and the like. And the pharmaceutical carriers for oral administration may include those suited for tables and capsules.

The compound of the present invention can be administered in an amount of 0.001–10 mg/kg/day, which may be given in one dosage or in divided doses and may be adjusted depending on various factors such as the severity of the symptoms, gender or age of a patient. A preferred single dosage of the compound of the present invention is from about 1 $\mu$g to about 600 mg.

The following examples are intended to illustrate the present invention more specifically, without limiting the scope of the invention.

PREPARATIVE EXAMPLE 1

Synthesis of 2-(3,4-dimethylphenoxy)ethylamine
[Method A]

(Step 1) Synthesis of ethyl (3,4-dimethylphenoxy)acetate 5.00 g (40.9 mmol) of 3,4-methylphenol and 4.4 ml(40.9 mmol) of ethyl chloroacetate were dissolved in 80 ml of acetone. To the resulting solution, 11.30 g(81.8 mmol) of calcium carbonate was added, and the mixture was refluxed for 48 hours. Thereafter, 100 ml of water were added thereto, and extracted with ether. The organic layer was washed with an aqueous 10% sodium hydroxide solution, dried and the solvent was evaporated under a reduced pressure to produce a residue, which was distilled under a reduced pressure to obtain 4.25 g (yield 53%) of the title compound as a colorless oil.

B.P.(boiling point): 80–85° C./0.25 mmHg. $^1$H NMR (CDCl$_3$, 200 MHz) $\delta$ 1.30(t, J=7.2 Hz, 3H, CH$_3$), 2.19(s, 6H, CH$_3$), 4.25(q, J=7.2 Hz, 2H, CH$_2$CH$_3$), 4.58(s, 2H, OCH$_2$), 6.61–7.05(m, 3H, ArH).

(Step 2) Synthesis of (3,4-dimethoxyphenoxy)acetic acid

To 4.48 g(21.5 mmol) of ethyl (3,4-dimethylphenoxy)-acetate as obtained in step 1 were added 3.44 g of sodium hydroxide and 100 ml of water. The resultant mixture was refluxed for 5 hours, acidified with hydrochloric acid, and extracted with ether (150 ml×2) and then washed with 100 ml of water. The organic layer was dried and the solvent was evaporated under a reduced pressure to obtain 3.17 g (yield 81%) of the title compound as a white solid.

M.P. (Melting Point): 158–160° C.; $^1$H NMR(DMSO-d$_6$, 200 MHz) $\delta$ 2.08(s, 6H, CH$_3$), 4.59(s, 2H, OCH$_2$), 6.58–7.03(m, 3H, ArH).

(Step 3) Synthesis of (3,4-dimethylphenoxy)acetamide

To 3.14 g (17.4 mmol) of (3,4-dimethylphenoxy)acetic acid obtained in step 2 were added 5.1 ml of thionyl chloride and 20 ml of dichloromethane. The resultant mixture was refluxed for 24 hours and the excess thionyl chloride and dichloromethane were removed by evaporating under a reduced pressure. The residue was dissolved in 30 ml of ether and 30 ml of aqueous ammonia was slowly added thereto at 0° C. After the resultant solution was stirred at an ambient temperature for 3 hours, the organic layer was separated. The aqueous layer was extracted with dichloromethane (50 ml×3). The organic layers were combined, dried and the solvent was evaporated under a reduced pressure to produce a residue, which was recrystallized from dichloromethane and hexane to obtain 2.53 g (yield 80%) of the title compound in a white colored solid.

M.P.: 127–129° C. $^1$H NMR(CDCl$_3$, 200 MHz) δ 2.20(s, 6H, 2ArCH$_3$), 4.47(s, 2H, OCH$_2$), 5.70(br s, 2H, NH$_2$), 6.63–7.08 (m, 3H, ArH).

(Step 4) Synthesis of (3,4-dimethylphenoxy)ethylamine 2.50 g (13.9 mmol) of (3,4-dimethylphenoxy)acetamide obtained in step 3 was dissolved in 50 ml of dry tetrahydrofuran, and added slowly to a solution of 1.05 g (27.8 mmol) of LiAlH$_4$ in 70 ml of dry tetrahydrofuran. The reaction mixture was refluxed for 5 hours and then 5 ml of water and 5 ml of 1N sodium hydroxide were added to decompose the remaining LiAlH$_4$. The resultant mixture was passed through a Celite™ layer and the filtrate was evaporated under a reduced pressure to produce a residue, which was distilled under a reduced pressure to obtain 0.63 g (yield 28%) of the title compound as a colorless oil.

B.P.: 110–115° C./0.75 mmHg.

$^1$H NMR(CDCl$_3$, 200 MHz) δ 2.08(s, 6H, CH$_3$), 3.60(t, J=6.4 HZ, 2H, CH$_2$Br), 4.24(t, J=6.4 Hz, 2M, OCH$_2$), 6.61–7.04(m, 3H, ArH).

[Method B]

(step 1') Synthesis of 1-bromo-2-(3,4-dimethylphenoxy)ethane 12.21 g (0.1 mol) of 3,4-dimethylphenol was dissolved in 500 ml of dry tetrahydrofuran and thereto added were 80 ml of 1,2-dibromoethane and then 14.4 g of NaH. The NaH was added in three divided amounts. The reaction mixture was refluxed for 48 hours and 200 ml of dichloromethane was added thereto. The resultant mixture was passed through a Celite™ layer and the filtrate was washed with a 10% aqueous sodium hydroxide solution (100 ml×3) and then concentrated under a reduced pressure. The resultant residue was purified by cromatography (eluent; ethyl acetate: hexane=1:6) to obtain 18.78 g (yield 82%) of the, title compound as a brown oil.

$^1$H NMR(CDCl$_3$, 200 MHz) δ 2.05(s, 6H, 2ArCH$_3$), 3.57(t, J=5.1 Hz, 2H, CH$_2$Br), 4.14(t, J=5.1 Hz, 2H, OCH$_2$2, 6.63–7.06(m, 3H, ArH)

(Step 2') Synthesis of 2-(3,4-dimethylphenoxy)ethylazide 18.7 g (81.6 mmol) of 1-bromo-2-(3,4-dimethylphenoxy)-ethane obtained in step 1' was dissolved in 500 ml of benzene. Thereto were added 1.85 g of NaN$_3$ and 8.40 g of n-Bu$_4$NBr, and the mixture was retfluxed for 24 hours, washed with water and concentrated under a reduced pressure. The resultant residue was purified by chromatography (eluent; ethyl acetate: hexane=1:9) to obtain 14.91 g (yield 96%) of the title compound as a brown oil.

$^1$H NMR(CDCl$_3$, 200 MHz) δ 1.54(br s, 6, 2H, NH$_2$), 2.16(s, 6H, 2ArCH$_3$), 3.06(t, J=5.3 Hz, 2H, CH$_2$N$_3$), 3.98(t, J=5.3 Hz, 2H, OCH$_2$), 6.64–7.05(m, 3H, ArH).

(Step 3') Synthesis of 2-(3,4-dimethylphenoxy)ethylamine 7.45 g (38.9 mmol) of 2-(3,4-dimethylphenoxy) ethylazide obtained in step 2' was dissolved in 200 ml of ethyl acetati and 12.44 g of 10% Pd/C was added thereto to carry out a hydrogenation reaction at a hydrogen pressure of 40 psi for 3 hours. The reaction mixture was passed through a Celite™ layer to remove Pd/C, concentrated at a reduced pressure to produce a residue, which was distilled under a reduced pressure to obtain 3.44 g (yield 53%) of the title compound as a colorless oil.

PREPARATIVE EXAMPLE 2

Synthesis of 3-(3,4-dimethylphenoxy)propylamine (Step 1) Synthesis of 1-chloro-3-(3,4-dimethylphenoxy)propane 6.12 g (50 mmol) of 3,4-dimethylphenol was dissolved in 150 ml of acetone. To the resulting solution were added 24.8 ml for 1-bromo-3-chloropropane and 20.7 g of K$_2$CO$_3$ and refluxed for 24 hours. To the reaction mixture was added 200 ml of water and extracted with dichloromethane (200 ml×3). The combined organic layer was washed with 100 ml of 1N sodium hydroxide and then with 200 ml of water, dried and the solvent was evaporated under a reduced pressure. The residue was distilled under a reduced pressure to obtain 9.1 g (yield 92%) of the title compound as a colorless oil.

B.P.: 78–80° C./0.45 umHg. $^1$H NMR(CDCl$_3$, 200 MHz) δ 2.16(s, 8H, 2ArCH$_3$, CH$_2$), 3.71(t, J=6.4 Hz, 2H, CH$_2$Cl), 4.05(t, J=5.9 Hz, 2H, OCH$_2$), 6.64–7.02(m, 3H, ArH).

(Step 2) Synthesis of 3-(3,4-dimethylphenoxy)propylazide 9.05 (45.6 mnol) of 1-chloro-3-(3,4-dimethylphenoxy)-propane obtained in step 1 was dissolved in 200 ml of toluene. To the resulting solution were added 14.8 g of NaN$_3$, 2.9 g of n-Bu$_4$ NBr and 15.2 g of KI and the mixture was refluxed For 24 hours. The reaction mixture was washed with water and concentrated under a reduced pressure. The resulting residue was purified by chromatography (ethyl acetate: hexane=1:10) to obtain 9.04 g (yield 97%) of the title compound as a brown oil.

$^1$H NMR(CDCl$_3$, 200 MHz) δ 2.05(q, J=6.0 Hz, 2H, CH$_2$), 2.19(s, 3H, CH$_3$), 2.23(s, 3H, CH$_3$), 3.50(t, J=6.3 Hz, 2H, CH$_2$N$_3$), 4.01(t, J=6.3 Hz, 2H, OCH$_2$), 6.62–7.05(m, 3H, ArH).

(Step 3) Synthesis of 3-(3,4-dimethylphenoxy)propylamine 6.20 g (30.2 mmol) of 3-(3,4-dimethylphenoxy) propylazide obtained in step 2 was dissolved in 150 ml of ethyl acetate and then 4.99 g of 5% Pd/C was added thereto to carry out a hydrogenation reaction at a hydrogen pressure of 40 psi for 30 minutes. The reaction mixture was passed through a Celite™ layer to remove Pd/C, concentrated under a reduced pressure to produce a residue, which was distilled under a reduced pressure to obtain 2.59 g (yield 48%) of the title compound as a colorless oil.

B.P.: 110–115° C./0.65 mmHg. $^1$H NMR(CDCl$_3$, 200 MHz) δ 1.35(br s, 2H, NH$_2$), 1.90(q, J=6.5 Hz, 2H, CH$_2$), 2.18(s, 3H, CH$_3$), 2.22(s, 3H, CH$_3$), 2.89(t, J=6.8 Hz, 2H, CH$_2$NH$_2$), 4.03(t, J=6.1 Hz, 2H, OCH$_2$), 6.62–7.03 (m, 3H, ArH).

PREPARATIVE EXAMPLE 3

Synthesis of 2-(3,4-dimethylbenzyloxy)ethylamine (Step 1) Synthesis of 3,4-dimethylbenzyloxyethanol 3.77 g(18.9 mmol) of 3,4-dimethylbenzylbromide and 1.27 g (22.7 mmol) of potassium hydroxide were dissolved in 2 ml of water and 5.88 g of ethylene glycol were slowly added thereto. The mixture was reacted at 100° C. for 7 hours. 100 ml of water was added to the reaction mixture, and the resulting solution was washed with ether (30 ml×3), dried and filtered under a reduced pressure. The filtrate was purified by chromatography (eluent; ethyl acetate: hexane=1:2) to obtain 2.32 g (yield 68%) of the title compound as a colorless oil.

¹H NMR(CDCl₃, 200 MHz) δ 2.14(t, J=5.9 Hz, 1H, OH), 2.25(s, 6H, CH₃), 3.58(t, J=3.5 Hz, 2H, OCH₂), 3.72(t, J=5.3 Hz, 2H, CH₂O), 4.49(s, 2H, ArCH₂), 7.02–7.13(m, 3H, ArH). Mass 180(M+), 165, 135, 119.

(Step 2) Synthesis of 2-(3,4-dimethylbenzyloxy)ethylazide 2.32 g (12.9 mmol) of 3,4-dimethylbenzyloxyethanol obtained in step 1 and 3.6 ml (26 mmol) of triethylamine were dissolved in 20 ml of dichloromethane and the resulting mixture was stirred at 0° C. for 30 minutes. 1.5 ml (19 mmol) of methanesulfonyl chloride was slowly added thereto. The mixture was stirred at 0° C. for 1 hour and then washed with an excess amount of water. The organic layer was dried and evaporated undter a reduced pressure to obtain 3.11 g (yield 94%) of a yellow oil, which was subsequently dissolved in 15 ml of DMSO and 3.91 g (60.2 mmol) of NaN₃ was added thereto to carry out a substitution reaction at 100° C. for 1 hour. After the addition of an excess amount of water, the reaction solution was extracted with 30 ml of dichloromethane three times. The combined organic layer was washed with water several times until DMSO was completely removed, dried and the solvent was evaporated under a reduced pressure. The residue was purified by chromatography (eluent; ethyl accetate: hexane=1:5) to obtain 2.29 g (yield 93%) of the title compound as a light yellow oil.

¹H NMR(CDCl₃, 200 MHz) δ 2.24(s, 6H, CH₃), 3.37(t, J=5.0 Hz, 2H, CH₂N₃), 3.61(t, J=5.0 Hz, 2H, OCH₂), 4.49(s, 2H, ArCH₂), 7.07–7.11(m, 3H, ArH). Mass 205(M+), 176, 162, 119 IR 1002, 2031, 2896, 3106 cm⁻¹

(Step 3) Synthesis of 2-(3,4-dimethylbenzyloxy)ethylamine 2.29 g (11.2 mmol) of 2-(3,4-dimethylbenzyloxy)ethylazide obtained in step 2 was dissolved in 15 ml of isopropanol while stirring, and 3.1 ml (22 mmol) of triethylamine was added thereto. The mixture was added to an isopropanol solution containing 1.1 ml (11 mmol) of 1,3-propanediol and then 4.22 g (0.11 moles) of NaBH₄ was added thereto. The mixture was stirred at an ambient temperature for 1 hour and the solvent was distilled off under a reduced pressure. The residue was dissolved in 10% aqueous citric acid and the resulting solution was washed three times with 30 ml of ether: hexane (1:1). The pH of the aqueous layer was adjusted to 12 with a 6N sodium hydroxide solution and then a saturated sodium chloride solution was added thereto. Thee aqueous layer was extracted with 30 ml of dichloromethane 3 times. The organic layer was dried and the solvent was evaporated under a reduced pressure to obtain 1.49 g (yield 75%) of the title compound as a colorless oil.

¹H NMR(CDCl₃, 200 MHz) δ 2.25(s, 6H, CH₃), 2.90(t, J=5.2 Hz, 2H, CH₂N), 3.27(s, 2H, NH₂), 3.52(t, J=5.3 Hz, 2H, OCH₂), 4.46(s, 2H, ArCH₂), 7.03–7.12(m, 3H, ArH).

PREPARATIVE EXAMPLE 4

Synthesis of 2-(4-methylthiophenoxy)ethylamine (Step 1) Synthesis of N-(2-bromoethyl)phthalimide 10 g (67.9 mmol) of phthalimide and then 11.3 g of potassium carbonate were dissolved in 117 ml of 1,2-dibromoethane. The resultant mixture was refluxed for 5 hours and 200 ml of water was added thereto. The reaction mixture was extracted with dichloromethane (150 ml×3) and the product was recrystallized from ethyl ether to obtain 8.9 g (yield 52%) of the title compound as a light yellow solid. TLC R₁ =0.4(eluent; ethyl acetate: hexane=1:6) M.P.: 79–80° C.; ¹H NMR(CDCl₃, 200 MHz) δ 3.16(t, J=6.7 Hz, 2H, NCH₂), 4.11(t, J=6.7 Hz, 2H, BrCH₂), 7.71–7.90(m, 4H, ArH).

(Step 2) Synthesis of 2-(4-methylthiophenoxy)ethylphthalimide 1.04 g (43.4 mmol) of NaH was dissolved in 40 ml of tetrahydrofuran at 0° C. To the resulting solution, 4 ml of 4-methylthiophenol dissolved in dry tetrahydrofuran was added slowly. The resultant mixture was stirred at an ambient temperature for 20 minutes and 8.0 g (31 mnol) of N-(2-bromoethyl)phthalimide obtained in step 1 dissolved in dry tetrahydrofuran was added. The mixture was stirred overnight at an ambient temperature and then refluxed for 2 hours. The reaction mixture was distilled under a reduced pressure to produce a residue, which was dissolved in dichloromethane. Then, the resultant solution was washed with water and with an aqueous sodium chloride solution. The organic layer was dried and dichloromethane was removed under a reduced pressure. The residue was recrystallized from a mixture of ethyl acetate/hexane to obtain 6.86 g of the title compound as a yellow solid. The solution remaining after the recrystallization was purified by column chromatography (eluent; ethyl acetate: hexane=1:6) to obtain additional 1.40 g of the title compound. Therefore, a total of 8.26 g (yield 90%) of the title compound was obtained.

TLC R₁=0.55(ethyl acetate: hexane=1:6) M.P. :/76–78° C.; ¹H NMR(CDCl₃, 200 MHz) δ 2.25(s, 3H, ArCH₃), 3.20(q, J=4.6 Hz, 2H, NCH₂), 3.92(t, J=6.9 Hz, 2H, SCH₂), 7.03–7.35(m, 4H, ArH).

(Step 3) Synthesis of 2-(4-methylthiophenoxy)ethylamine 5.00 g (16.8 mmol) of 2-(4-methylthiophenoxy)ethylphthalimide obtained in step 2 was dissolved in 160 ml of ethanol and 4 ml(80 mmol) of 80% hydrazine was added thereto. Then, the resultant mixture was refluxed for 2 hours and 20 ml of methanolic HCl was added thereto. Then, the reaction mixture was filtered to remove by-products and the solvent was removed under a reduced pressure to produce a residue. The pH of the residue was adjusted to 10–11 with an 1N sodium hydroxide aqueous solution and the resultant was dissolved in ethyl ether. The resulting solution was washed with an aqueous sodium chloride solution, dried and the solvent was evaporated under a reduced pressure to obtain 2.31 g (yield 82%) of the title compound as a yellow oil.

TLC R$_f$=0.3(eluent; ethyl acetate: hexane=1:4) M.P. of HCl salt: 125–129° C.; ¹H NMR(CDCl₃, 200 MHz) δ 1.51(s, 2H, NH₂), 2.32(s, 3H, ArCH₃), 2.83–3.01(m, 4H, CH₂NH₂, SCH₂), 7.06–7.32(m, 4H, ArH).

PREPARATIVE EXAMPLE 5

Synthesis of 2-(3,4-dimethylthiophenoxy) ethylamine

The procedure of Preparative Example 4 was repeated except that 3,4-dimethylthiophenol was employed in place of 4-methylthiophenol to obtain 2.00 g of the title compound.

¹H NMR(CDCl₃, 200 MHz) δ 1.51(s, 2H, NH₂), 2.25(s, 6H, 2CH₃), 2.85–3.02(m, 4H, 2CH₂), 7.05–7.19(m, 3H, ArH).

EXAMPLE 1

Synthesis of N-{2-(3,4-dimethylphenoxy)ethyl}-4-(2-aminoethoxy)-3-methoxyphenylacetamide (Step 1) Synthesis of N-{2-(3,4-dimelthylphenoxy)ethyl}-4-hydroxy-3-methoxyphenylacetamide 9.52 g (57.6 mmol) of 2-(3,4-dimethylphenoxy) ethylamine obtained in preparative Example 2, 10.55 g (58.0 mmol) of 4-hydroxy-3-methoxyphenylacetic acid and 11 g of powdered 4A molecular sieve 4A were mixed and the resulting mixture was reacted at 1.50–160° C. for 5 hours. Thereafter, the reaction mixture was dissolved in 20 ml of dichloromethane and then purified by chromatography (eluent; ethyl acetate: hexane=1:4) to obtaiin 14.36 g (yield 76%) of the title compound as a white solid.

M.P.: 103–104° C.; $^1$H NMR(CDCl$_3$, 200 MHz) δ 2.19(s, 6H, 2ArCH$_3$), 3.50(s, 2H, COCH$_2$), 3.60(q, J=5.4 Hz, 2H, NHCH$_2$), 3.80(s, 3H, OCH$_3$), 3.96(t, J=5.0 Hz, 2H, OCH$_2$), 5.61(br s, 1H, NH), 5.90(br s, 1H, OH), 6.61–7.03(m, 6H, ArH); Mass 330(M+), 209, 208, 138, 137, 44; Elemental Analysis as for C$_{19}$H$_{23}$NO$_4$ (calculated/measured): C(69.32/68.91), H(6.99/6.98), N(4.25/4.14).

(Step 2) Synthesis of N-{2-(3,4-diemthylphenoxy)ethyl}-4-(2-bromoethoxy)-3-methoxyphenylacetamide 14.56 g (44.2 mmol) of N-{2-(3,4-dimelthylphenoxy)ethyl}-4-hydroxy-3-methoxyphenylacetamide obtained in step 1 and 54.1 ml of 1,2-dibromoethane were added to 500 ml of dry tetrahydrofuran, followed by adding 8.5 g of 50% NaH thereto. The resulting mixture was refluxed for 27 hours. After the addition of 200 ml of water, the reaction mixture was extracted with dichloromethane (150 ml×3) and the organic layer was dried and concentrated under a reduced pressure to produce a residue, which was purified by chromatography (ethyl acetate: hexane=1:4) to obtain 9.07 g (yield 47%) of the title compound as a white solid.

M.P.: 105–106° C.; $^1$H NMR(CDCl$_3$, 200 MHz) δ 2.18(s, 6H. 2ArCH$_3$), 3.52(s, 2H, COCH$_2$), 3.52–3.69(m, 4H, NHCH$_2$, OCH$_2$), 3.80(s, 3H, OCH$_3$), 3.97(t, J=5.4 Hz, 2H, OCH$_2$), 4.32(t, J=6.7 Hz, 2H, CH$_2$Br), 5.91(br s, 1H, NH), 6.58–7.04(m, 6H, ArH) Mass 435(M+), 317, 316, 315, 314, 245, 243, 137, 44.

(Step 3) Synthesis of N-{2-(3,4-dimelthylphenoxy)ethyl}-4-(2-azidoethoxy)-3-methoxyphenylacetamide 8.97 g (20.5 mnol) of N-{2-(3,4-dimelthylphenoxy)ethyl}-4-(2-bromoethoxy)-3-methoxyphenylacetamide obtained in step 2 was dissolved in 500 ml of benzene and thereto were added 6.42 g (0.012 mmol) of NaN3 and 1.27 g (5.13 mmol) of n-Bu$_4$NBr, and the mixture was refluxed for 24 hours, After the addition of 200 ml of water, the reaction mixture was extracted with dichloromethane. The combined organic layer was dried and concentrated under a reduced pressure to produce a residue, which was purified by chromatography (ethyl acetate: hexane=1:1) and recrystallized from dichloromethane/hexane to obtain 8.05 g (yield 99%) of the title compound as a white solid.

M.P.: 95–97° C.; $^1$H NMR(CDCl$_3$, 200 MHz) δ 2.18(s, 6H, 2ArCH$_3$), 3.50(s, 2H, COCH$_2$), 3.58–3.75(m, 4H, NHCH$_2$OCH$_2$), 3.79(s, 3H, OCH$_3$), 3.93(t, J=6.0 Hz, 2H, OCH$_2$), 4.16(t, J=5.2 Hz, 2H, CH$_2$N$_3$), 5.90(br s, 1H, NH), 6.63–7.05(m, 6H, 2ArH).

(Step 4) Synthesis of N-{2-(3,4-dimethylphenoxy)ethyl}-4-(2-aminoethoxy)-3-methoxyphenylacetamide 1.00 g (2.5 mmol) of N-{2-(3,4-dimethylphenoxy)ethyl}-4-(2-azidoethoxy)-3-methoxyphenylacetamide obtained in step 3 was dissolved in 100 ml of methanol and thereto was added 0.40 g of 10% Pd/C. The mixture was stirred under a hydrogen atmosphere at an ambient temperature for 5 hours. The reaction mixture was passed through a Celite™ layer to remove Pd/C, and the filtrate was concentrated under a reduced pressure to produce a residue, which was recrystallized form dichloromethane/hexane to obtain 0.60 g (yield 64%) of the title compound as a white solid.

M.P.: 90–92° C.; $^1$H NMR(CDCl$_3$, 200 MHz) δ 1.49(br s, 2H, NH$_2$), 2.13(s, 6H, 2ArCH$_3$), 3.08(t, J=5.4 Hz, 2H, CH$_2$NH$_2$), 3.46(s, 3H, COCH$_3$), 3.56(q J=5.6 Hz, 2H, NHCH$_2$), 3.77(s, 3H, OCH$_2$), 3.94(t, J=5.0 Hz, 2H, OCH$_2$), 4.04(t, J=5.4 Hz, 2H, OCH$_2$), 5.90(br s, 1H, NH), 6.60–7.01 (m, 6H, 2ArH); Mass 3–2(M+), 251, 209, 208, 148, 137, 44; Elemental Analysis for C$_{21}$H$_{28}$N$_2$O$_4$(calculated/measured): C(67.7/65.90), H(7.52/7.37), N(7.52/7.34).

EXAMPLE 2

Synthesis of N-{3-(3,4-dimethylphenoxy)propyl}-4-(2-aminoethoxy)-3-methoxyphenylacetamide (Step 1) Synthesis of N-{3-(3,4-dimethylphenoxy)propyl}-4-(2-azidoethoxy)-3-methoxyphenylacetamide 3.80 g (15.1 mmol) of 4-(2-azidoethoxy)-3- methoxyphenylacetic acid was dissolved in 100 ml of dichloromethane and thereto was added 2.5 ml of oxalyl chloride. The resultant mixture was refluxed for 3 hours and then the solvent was removed to obtain 3.90 g of acid chloride. 2.58 g (14.4 mmol) of 3-(3,4-dimelthylphenoxy)propylamine obtained in Preparative Example 2 was dissolved in 100 ml of dichloromethane and t This solution was added dropwise to a solution of the acid chloride prepared above in 100 ml of dichloromethane at a temperature of 0–5° C. 10 minutes later, 2.4 ml of triethylamine was added and stirred overnight at an ambient temperature. The reaction mixture was washed successively with 200 ml of 1N hydrochloric acid, 200 ml of water, 200 ml of 1N NaOH and then 150 ml of water. The organic layer was dried and the solvent was evaporated under a reduced pressure to produce a residue, which was recrystallized from dichloromethane/hexane to obtain 4.68 g (yield 79%) of the title compound as a white crystal.

M.P.: 103–106° C.; $^1$H NMR(CDCl$_3$, 200 MHZ) δ 1.92(q, J=5.4 Hz, 2H, CH$_2$), 2.19(s, 3H, CH$_3$), 2.22(s, 3H, CH$_3$), 3.44(q, J=5.0 Hz, 2H, NHCH$_3$), 3.51(s, 2H, CH$_2$O), 3.64(t, J=5.0 Hz, 2H, CH$_2$N$_3$), 3.80(s, 3H, OCH$_3$), 3.93(t, J=5.8 Hz, 2H, OCH$_2$), 4.11(t, J=5.2 Hz, 2H, OCH$_2$), 5.85(br s, 1H, NH), 6.48–7.03(m, 6H, ArH); Mass 412(M+), 292, 291, 222.

(Step 2) Synthesis of N-{3-(3,4-dimethyphenoxy)propyl}-4-(2-aminoethoxy)-3-methoxyphenylacetamide 2.00 g (4.9 mmol) of N-{3-(3,4-dimethylphenoxy)propyl}-4(2-azidoethoxy)-3-methoxyphenylacetamide obtained in step 1 was dissolved in 150 ml of ethyl acetate and thereto was added 0.62 g of 5% Pd/C to carry out an hydrogenation reaction under hydrogen atmosphere for 5 hours. Then, the reaction mixture was passed through a Celite™ layer to remove Pd/C and the filtrate was concentrated under a reduced pressure to produce a residue, which was recrystallized from dichloromethane/hexane to obtain 1.62 g (yield 86%) of the litle compound as a white crystal.

M.P.: 104–106° C.; $^1$H NMR(CDCl$_3$, 200 MHz) δ 1.62(br s, 2H, NH$_2$), 1.91(q, J=6,2 Hz, 2H, CH$_2$) 2.18(s, 3H, CH$_3$), 2.21(s, 3H, CH$_3$), 3.07(t, J=5.4 Hz, 2H, CH$_2$NH$_2$), 3.46(q, J=6.2 Hz, 2H, NHCH$_2$), 3.50(s, 2H, CH$_2$CO), 3.81(s, 3H, OCH$_3$), 3.92(t, J=5.8 Hz, 2H, OCH$_2$), 4.03(t, J=5.2 Hz, 2H, CH$_2$O), 5.83(br s, 1H, NH), 6.48–7.01(m, 6H, ArH); Mass 386(M+), 265, 222; Elemental Analysis for C$_{22}$H$_{30}$N$_2$. ½ H$_2$O (calculated/measured): C(66.83/66.47), H(7.84/7.58), N(7.08/6.92).

EXAMPLE 3

Synthesis of N-{2-(3,4-dimethylbenzyloxy)ethyl}-4-(2-aminoethoxy)-3-methoxyphenylacetamide (Step 1) Synthesis of N-{2-(3,4-dimethylbenzyloxy)ethyl}-4-(2-azidoethoxy)-3-methoxyphenylacetamide 1.49 g (8.31mmol) of 2-(3,4-dimethylbenzyloxy) ethylamine obtained in Preparative Example 3 and 2.30 g (9.14 mmol) of 4-(2-azidoethoxy)-3-methoxyphenylacetic acid were dissolved in 25 ml of acetonitrile. The resulting mixture was cooled to 0° C., and 2.06 g (9.97 mmol) of dicyclocarbodiimide was added thereto. The temperature of the reaction mixture was slowly elevated to an ambient temperature and then the mixture was stirred for 4 hours and filtered. The filtrate was concentrated under a reduced pressure to produce a residue, which was purified by chromatography (eluent; ethyl acetate: hexane=2:1) to obtain 2.70 g (yield 79%) of the title coompound as a white solid.

M.P.: 75–77° C.; $^1$H NMR(CDCl$_3$, 200 MHz) δ 2.25(s, 6H, 2CH$_3$), 3.43(t, J=4.1 Hz, 2H, NCH$_2$), 3.47(t, J=6.5 Hz, 2H, OCH$_2$), 3.49(s, 2H,COCH$_2$), 3.62(t, J=5.2 Hz, 2H, OCH$_2$), 3.72(s, 3H, OCH$_3$), 4.15(t, J=5.2 Hz, 2H, CH$_2$N$_3$), 4.38(s, 2H, OCH$_2$), 5.88(br s, 1H, NH), 6.73–7.12(m, 6H, ArH); Mass 413(M+1), 276, 235, 206, 190, 178.

(Step 2) Synthesis of N-{2-(3,4-dimethylbenzyloxy)ethyl}-4-(2-aminoethoxy)-3-methoxyphenylacetamide 2.70 g (6.54 mmol) of N-{2-(3,4-dimethylbenzyloxy)ethyl}-4-(2-azidoethoxy)-3-methoxyphenylacetamide obtained in step 1 was dissolved in 100 ml of isopropanol and 1.82 ml (13.31 mmol) of ethylamine was added thereto with stirring. 66 ml(6.54 1nmol) of 1,3-propanedithiol was dissolved in isopropanol to a concentration of 0.1M, to which the solution prepared above and 2.48 g (6.54 mmol) of NaBH$_4$ were slowly added. The resulting mixture was stirred at an ambient temperature for 1 hour and then the solvent was removed under a reduced pressure to produce a residue, which was dissolved in 10% citric acid. The resulting solution was washed with 30 ml of a mixture of ether: hexane (1:1) three times. The pH of the aqueous layer was adjusted to 12 with sodium hydroxide solution, and a saturated sodium chloride solution was added thereto. The resultant was extracted with 30 ml of dichloromethane 3 times and the organic layer was dried and concentrated under a reduced pressure to produce a solid, which was recrystallized from ethyl acetate/hexane to obtain 1.82 g (yield 72%) of the title compound as a white solid.

M.P.: 60–62° C.; $^1$H NMR(CDCl$_3$, 200 MHz) δ 2.25(s, 6H, 2CH$_3$), 3.10(t, J=5.3 Hz, 2H, NCH$_2$) 3.41–3.51(m, 6H, NCH$_2$, OCH$_2$COCH$_2$), 3.81(s, 3H, OCH$_3$), 4.02(t, J=5.3 Hz, 2H, OCH$_2$), 4.38(s, 2H, ArCH$_2$), 5.88(br s, 1H, NH), 6.73–7.12(m, 6H, ArH)

Mass 386(M+), 252, 209, 138.

EXAMPLE 4

Synthesis of N-{2-(3,4-dimethylbenzyloxy)ethyl}-4-hydroxy-3-methoxyphenylacetamide 0.82 g (4.57 mmol) of 2-(3,4-dimethylbenzyloxy)ethanolamine obtained in Preparative Example 3 and 0.92 g (5.03 mmol) of 4-hydroxy-3-methoxyphenylacetic acid were dissolved in 50 ml of acetonitrile. The resulting mixture was cooled to 0° C., and 1.04 g (5.03 mmol) of dicyclohexylcarbodiimide was added thereto. The temperature of the mixture was slowly elevated to an ambient temperature and then stirred for 4 hours. The resultant was filtered and the filtrate was concentrated under a reduced pressure to produce a residue, which was purified by a column chromatography (eluent; methanol: ethyl acetate: hexane=1:16:16) and recrystallized from dichloromethane/hexane to obtain 1.17 g (yield 75%) of the title compound as a white solid.

M.P.: 82–83° C.; $^1$H NMR(CDCl$_3$, 200 MHz) δ 2.25(s, 6H, 2CH$_3$), 3.4–3.46(m, 4H, OCH$_2$, NCH$_2$), 3.48(s, 2H, COCH$_2$), 3.84(s, 3H, OCH$_3$), 4.36(s, 2H, OCH), 5.60(s, 1H, OH), 5.83(br s, 1H, NH), 6.70–7.11(m, 6H, ArH); Mass 343(M+), 264, 223, 209, 138.

EXAMPLE 5

Synthesis of N-{2-(4-methylthiophenoxy)ethyl}-4-(2-aminoethoxy)-3-methoxyphenylacetamide (Step 1) Synthesis of N-{2-(4-methylthiophenoxy)ethyl}-4-(2-azidoethoxy)-3-methoxyphenylacetamide 2.00 g (12.0 mmol) of 2-(4-methylthiophenoxy)ethylamine obtained in Preparative Example 4 was dissolved in 30 ml of dry tetrahydrofuran and the resultant solution was mixed with a solution obtained by dissolving 3.13 g (13.2 mmol) of 4-(2-azidoethoxy)-3-methoxyphenylacetic acid in 100 ml of dry tetrahydrofuran. After the addition of 3.47 g of dicyclohexylcarbodiimide (DCC), the reaction mixture was allowed to stand at an ambient temperature, concentrated under a redured pressure to produce a residue, which was purified by a column chromatography (eluent; ethyl acetate: hexane=2:1) to obtain 3.24 g (yield 68%) of the title coumpound.

M.P.: 73–75° C.; $^1$H NMR(CDCl$_3$, 200 MHz) δ 2.30(s, 3H, ArCH$_3$), 2.95(t, J=6.4Hz, 2H, CH$_2$N$_3$), 3.85(s, 3H, OCH$_3$), 4.17(t, J=5.2 Hz, 2H, OCH$_2$), 5.80(s, 1H, NH), 6.71–7.25(m, 7H, ArH).

(Step 2) Synthesis of N-{2-(4-methylthiophenoxy)ethyl}-4-(2-aminoethoxy)-3-methoxyphenylacetamide 1.50 g (3.7 mmol) of N-{2-(4-methylthiophenoxy)ethyl}-4-(2-azidoethoxy)-3-methoxyphernylacetamide obtained in step 1 above was dissolved in 50 ml of methanol and thereto was added 0.91 g of 10% Pd/C to carry out a hydrogenation reaction at hydrogen pressure of 10 psi for one and a half hour. Then, the reaction mixture was passed through a Celite™ layer to remove Pd/C. The filtrate was concentrated under a reduced pressure to obtain a yellow oil, which was recrystallized from ethyl ether to obtain 1.4 g (yield 92%) of the title compound as a yellow solid.

TLC R$_f$=0.25(tbutanol:acetic acid:water=4:1:1); M.P.: 67–122° C.; $^1$H NMR(CDCl$_3$, 200 MHz) δ 1.60(s, 2H, NH$_2$), 2.32(s, 3H, ArCH$_3$), 2.97(t, J=6.2 Hz, 2H, SCH$_2$), 3.12(t, J=5.1 Hz, 2H, CH$_2$), 3.49(s, 2H, CH$_2$CO), 3.87(s, 3H, OCH$_3$), 4.06(t, J=5.1 Hz, 2H, OCH$_2$), 5.84(s, 1H, NH), 6.72–7.27(m, 7H, ArH)

EXAMPLE 6

Synthesis of N-{2-(3,4-dimethylthiophenoxy)ethyl}-4-(2-aminoethoxy)-3-methoxyphenylacetarnide The procedure of Example 5 was repeated except for using 2-(3,4-dinie-hylthiophenoxy)ethylamine obtained in Preparative Example 5 instead of 2-(4-ethylthiophenoxy)ethylamine to obtain the title compound.

M.P.: 85 to 87° C.; $^1$H NMR(CDCl$_3$, 200 MHz) δ 1.60(s, 2H, CH$_2$), 2.22(s, 6H, 2CH$_3$), 2.96(t, J=6.2 Hz, 2H, CH$_2$), 3.11(t, J=5.3 Hz, 2H, CH$_2$), 3.37(q, J=6.2 Hz, 2H, CH$_2$), 3.48(s, 2H, CH$_2$), 3.86(s, 3H, OCH$_3$), 4.04(t, J=5.3 Hz, 2H, CH$_2$), 5.88(br s, 1H, NH), 6.71–6.78(m, 2H, ArH), 6.87(d, J=7.9 Hz, 1H, ArH), 7.03–7.09(m, 3H, ArH)

Activity Test

The physiological activities of the compounds of the present invention prepared according to Example 1 to 6 were measured by employing acetic acid or phenyl-1,4-benzoquinone (PBQ) induced writhing test method.

1) Animals Tested

In case of the acetic acid-induced writhing test, KTC-ICR rats (available from animal laboratory of Korea Research Institute of Chemical Technology) each having a body weight of 20–25 g were used, while in the PBQ induced writhing test, KTC-ICR rats each having a body weight of 14–18 g were employed. A group consisting of 8 mice which had been adjusted to the testing environment for a week were used in determining the effects of each dosage of a test compound. Water and food were given frelly and illumination was maintained on a 12-hour cycle.

2) Testing Method

Test solutions were prepared by dissolving one of the final products obtained in Examples 1 to 6 in distilled water containing 1% of Tween and 5% ethanol in a pre-determined concentration. The test solutions were used after serial dilution depending on each dosage.

The test solutions were intraperitoneally administered in a dose of 0.1 ml per 10 g of a body weight. 0.1 ml of 1% acetic acid solution or 0.1 ml of 0.02% PBQ solution was administered after in case of oral administration or after 30 minutes in case of subcutaneous injection.

Then, the number of writhings generated during a period of 10 minutes after 3 minutes from the administration of acetic acid was measured. in case of the administration of PBQ, the number of writhings generated during a period of 5 minutes after 5 minutes from the administration was measured.

For a comparison purpose, initially, distilled water containing 1% of Tween and 5% ethanol alone was administered to the control group. Then, the control groups were subjeted the same procedure as the test groups.

3) Measurement of Analgesic Effect

The number of writhings suffered by the test group was compared with that of the control group; and the analgesic effect was measured in terms of the percentage of inhibition of writhing (I.W.).

$$I.W.\ (\%) = \frac{A - B}{A} \times 100$$

wherein:

A is the number of writhings suffered by the control group; and

B is the number of writhings suffered by the test group.

I.W. values for each dosage were calculated by employing regression analysis. The amount of a test compound which is required in reducing the frequency of writhings to the 50% level of that generated by the control group, i.e., B=0.5A or I.W.=50%, is designated as $ED_{50}$(mg/kg of a body weight). Therefore, a lower value of $ED_{50}$ represents a higher analgesic effect of the tested compound. These $ED_{50}$ values for the test compounds are shown in Table I.

TABLE I

| Compounds | $ED_{50}$ (mg/kg of a body weight) | |
|---|---|---|
| | acetic acid | PBQ |
| NE-19550[1] | 15.7 | |
| NE-21610[2] | >300 | 38.3 |
| Capsaicin[3] | 1.34 | |
| Phenylbutazone[4] | | 79.8 |
| Aspirin[5] | | 71.4 |
| Naproxen[6] | | 17.1 |
| Ibuprofen[7] | | 11.0 |
| Example 1 | | 9.53 |
| Example 2 | | 7.02 |
| Example 3 | | 10.95 |
| Example 4 | 2.08 | |
| Example 5 | 0.84 | |
| Example 6 | 0.48 | |

Notes:

TABLE I-continued

| Compounds | $ED_{50}$ (mg/kg of a body weight) | |
|---|---|---|
| | acetic acid | PBQ |

[1] N-vanillyloleamide (see EP 0 282 127)
[2] N-{4-(2-aminoethoxy)-3-methoxybenzyl}-oleamide (see EP 0 282 127)
[3] N-vanillyl-trans-8-methyl-6-nonenamide
[4]–[7] commercially available antiphlogistic analgesia As shown in Table 1, the compounds of the present invention have much lower $ED_{50}$ values than the conventional compounds, and therefore, they exhibit stronger analgesic activities.

Toxicity Test

In order to monitor harmful side-effects or toxicities of the present compounds, various behavioral changes in the test animals were observed. After the test and the control solutions were administered to the animals, symptoms such as sedation, ptosis, dyspnoea, vasodilation, convulsion, salivation and urination were observed and the level of such changes was represented by a numbering system: that is, the normal value of the last three behaviors(i.e., urination, convulsion and salivation) is 0; and that of the others(i.e., sedation, ptosis, dyspnoea and vasodilation) is 4. The higher the number is, the greater the side effects are.

The results of the test for some of the compounds are shown in Table II.

TABLE II

| Compounds | | Seda-tion | Pto-sis | Dysp-noea | Vaso-dila-tion | Con-vul-sion | Saliva-tion | Urina-tion |
|---|---|---|---|---|---|---|---|---|
| Ex. | Amount mg/kg | | | | | | | |
| 2 | 10 | 7 | 6 | 7 | 6 | 0 | 0 | 0 |
| | 5 | 6 | 6 | 5 | 5 | 0 | 0 | 0 |
| | 2.5 | 4 | 4 | 4 | 4 | 0 | 0 | 0 |
| 3 | 20 | 5 | 5 | 4 | 4 | 0 | 0 | 0 |
| | 10 | 4 | 4 | 4 | 4 | 0 | 0 | 0 |
| | 5 | 4 | 4 | 4 | 4 | 0 | 0 | 0 |
| 4 | 5 | 7 | 7 | 6 | 5 | 0 | 0 | 0 |
| | 2.5 | 6 | 6 | 5 | 4 | 0 | 0 | 0 |
| | 1.25 | 4 | 4 | 4 | 4 | 0 | 0 | 0 |
| 5 | 2.5 | 7 | 6 | 6 | 5 | 0 | 0 | 0 |
| | 1.25 | 6 | 6 | 6 | 4 | 0 | 0 | 0 |
| | 0.63 | 4 | 4 | 4 | 4 | 0 | 0 | 0 |
| 6 | 1.25 | 6 | 6 | 6 | 5 | 0 | 0 | 0 |
| | 0.63 | 6 | 5 | 4 | 4 | 0 | 0 | 0 |
| | 0.31 | 4 | 4 | 4 | 4 | 0 | 0 | 0 |
| Con-trol* | 1 | 7 | 7 | 6 | 6 | 1 | 0 | 0 |
| | 0.5 | 7 | 7 | 6 | 5 | 1 | 0 | 0 |
| | 0.25 | 6 | 6 | 5 | 5 | 1 | 0 | 0 |

*:Control compound: N-{3-(3,4-dimethylphenyl)propyl}-4-(2-aminoethoxy)-3-methoxyphenylacetamide (see U.S. Pat. No. 5,242,944)

As shown in Table 2, the compounds of the present invention exhibit side effect only when used in considerably larger amounts than the control. Therefore, the compounds of the present invention exhibit less toxicity.

Thus, the compounds of formula (I) of the present invention have higher analgesic and anti-inflammatory activities, while exhibiting much reduced irritability and toxicity.

While the invention has been described with respect to the specific embodiments, it should be recognized that various modifications and changes may be made by those skilled in the art to the invention which also fall within the scope of the invention as defined by the appended claims.

What is claimed is:

1. A phenylacetamide compound of formula (I) and a pharmaceutically acceptable salt thereof:

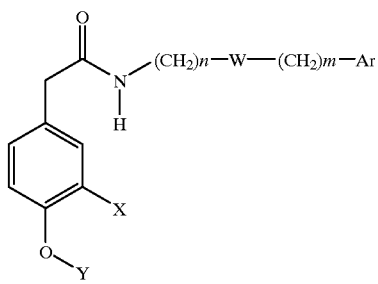

(I)

wherein:

X is hydrogen, halogen, hydroxy or $C_{1-3}$ alkoxy group; and

Y is hydrogen, $C_{3-5}$ hydroxyalkyl, $CH_2CH_2NR^1R^2$ wherein $R^1$ and $R^2$ are each independently hydrogen, $C_{1-3}$ alkyl, $C_{1-3}$ hydroxyalkyl, $C_{1-3}$ aminoalkyl, formyl, $C_{1-3}$ alkylcarbonyl or $C_{13}$ alkoxycarbonyl group;

Ar is phenyl or phenyl having one or more substituents selected from the group consisting of $C_{1-5}$ alkyl, halogen hydroxy, $C_{1-5}$ alkoxy and alkylenedioxy group;

W is an oxygen or sulphur atom;

n is an integer ranging from 1 to 5; and m is 0 or an integer ranging from 1 to 5.

2. The compound according to claim 1, wherein X is methoxy.

3. The compound according to claim 2, wherein Y is hydrogen or $CH_2CH_2NR^1R^2$ wherein $R^1$ and $R^2$ are each independently hydrogen or $C_{1-3}$ alkyl; A is phenyl or phenyl having one or two methyl substituents; n is 2, 3 or 4 and m is 0 or 1.

4. The compound according to claim 1, which is selected from the group consisting of:

N-{2-(3,4-dimethylphenoxy)ethyl}-4-(2-aminoethoxy)-3-methoxy-phenylacetamide;

N-{3-(3,4-dimethylphenoxy)propyl}-4-(2-aminoethoxy)-3-methoxyphenylacetamide;

N-{2-(3,4-dimethylbenzyloxy)ethyl}-4-(2-aminoethoxy)-3-methoxyphenylacetamide;

N-{2-(3,4-dimethylbenzyloxy)ethyl}-4-hydroxy-3-methoxyphenylacetamide;

N-{2-(4-methylthiophenoxy)ethyl}-4-(2-arinoethoxy)-3-methxomyphenylacetamide; and N-{2-(3,4-dimethylthiophenoxy)ethyl}-4-(2-aminoethoxy)-3-methoxyphenylacetamide.

5. A process for preparing an N-arylalkylhomovanillic amide derivative of formula (I) which comprises:

(i) reacting a compound of formula (II) with an amine compound of formula (III) to produce a compound of formula (IV), and (ii) reactinig the compound of formula (IV) with a compound suitable for constructing a desired substituent Y to providfe the compound (I):

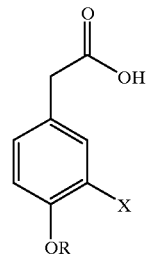

(II)

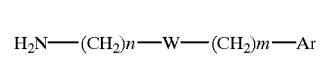

(III)

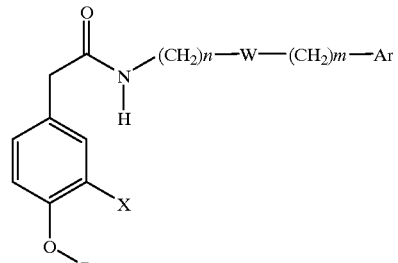

(IV)

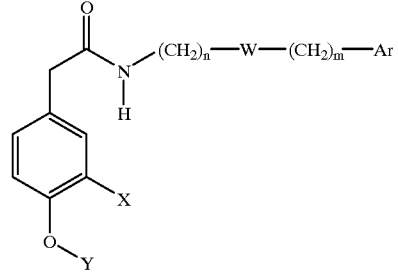

(I)

wherein:

R is H, $CH_2CH_2Cl$, $CH_2CH_2Br$, $CH_2CH_2N_3$ or $CH_2CH_2NH_2$; and m, n, W, X and Ar have the same meanings as defined in claim 1.

6. A pharmaceutical composition comprising an effective amount of the compound or the pharmaceutically acceptable salts thereof according to claim 1 as an active ingredient, and a pharmaceutical acceptable carrier.

* * * * *